(12) United States Patent
Braun et al.

(10) Patent No.: US 9,668,883 B2
(45) Date of Patent: Jun. 6, 2017

(54) TRIAL KIT FOR KNEE PROSTHESIS SYSTEM

(71) Applicant: DePuy Ireland Unlimited Company, Cork (IE)

(72) Inventors: Jordan T Braun, Napoleon, OH (US); Chadd W. Clary, Fort Wayne, IN (US); Abraham P Wright, Winona Lake, IN (US)

(73) Assignee: DEPUY IRELAND UNLIMITED COMPANY, Cork (IE)

( * ) Notice: Subject to any disclaimer, the term of this patent is extended or adjusted under 35 U.S.C. 154(b) by 35 days.

(21) Appl. No.: 14/830,072

(22) Filed: Aug. 19, 2015

(65) Prior Publication Data

US 2017/0049582 A1 Feb. 23, 2017

(51) Int. Cl.
*A61F 2/46* (2006.01)
*A61F 2/38* (2006.01)

(52) U.S. Cl.
CPC ............ *A61F 2/4684* (2013.01); *A61F 2/389* (2013.01); *A61F 2220/0025* (2013.01); *A61F 2220/0033* (2013.01)

(58) Field of Classification Search
CPC .................... A61F 2/4684; A61F 2/389; A61F 2220/0025; A61F 2220/0033
See application file for complete search history.

(56) References Cited

U.S. PATENT DOCUMENTS

| | | | |
|---|---|---|---|
| 5,782,925 A | 7/1998 | Collazo et al. | |
| 5,928,286 A | 7/1999 | Ashby et al. | |
| 5,976,147 A * | 11/1999 | LaSalle | A61B 17/1604 606/102 |
| 6,063,091 A * | 5/2000 | Lombardo | A61B 17/1735 606/102 |
| 6,942,670 B2 | 9/2005 | Heldreth | |
| 7,658,767 B2 | 2/2010 | Wyss | |
| 7,850,698 B2 | 12/2010 | Straszheim-Morley | |
| 8,092,545 B2 | 1/2012 | Coon et al. | |
| 8,366,782 B2 * | 2/2013 | Wright | A61F 2/30721 623/20.15 |
| 8,545,570 B2 * | 10/2013 | Crabtree | A61F 2/385 623/20.24 |
| 8,568,485 B2 * | 10/2013 | Ries | A61B 17/1764 623/20.29 |
| 8,939,986 B2 * | 1/2015 | Waite, II | A61B 17/1764 606/88 |

(Continued)

OTHER PUBLICATIONS

Coordinate Ultra Revision Knee System, Surgical Technique, 1997, p. 24.

(Continued)

*Primary Examiner* — Zade Coley (57) ABSTRACT

A trial kit for a hinged knee implant system is disclosed. The trial kit includes a tibial base plate trial, an adaptor and a tibial bearing insert trial. The adaptor and insert trial can be assembled and the assembly mounted on the tray trial by sliding the assembly in an anterior-posterior direction on the tray trial. The adaptor has a post with a cross-piece. The insert trial has openings and channels to receive the post and cross-piece. The openings are sized, shaped and oriented so that the cross-piece of the elongate post must be oriented in different directions to pass through the different openings.

10 Claims, 10 Drawing Sheets

(56) References Cited

U.S. PATENT DOCUMENTS

| | | | | |
|---|---|---|---|---|
| 8,968,412 | B2* | 3/2015 | Wogoman | A61F 2/4684 623/20.15 |
| 9,028,501 | B2 | 5/2015 | Thomas et al. | |
| 9,095,356 | B2 | 8/2015 | Thomas et al. | |
| 9,113,915 | B2* | 8/2015 | Thomas | A61B 17/157 |
| 9,216,089 | B2* | 12/2015 | Major | A61F 2/4684 |
| 2004/0153091 | A1* | 8/2004 | Figueroa | A61B 17/1764 606/102 |
| 2004/0225368 | A1* | 11/2004 | Plumet | A61F 2/3886 623/20.15 |
| 2006/0030945 | A1* | 2/2006 | Wright | A61F 2/30721 623/20.15 |
| 2008/0306603 | A1* | 12/2008 | Reich | A61F 2/389 623/20.15 |
| 2012/0158152 | A1 | 6/2012 | Claypool et al. | |
| 2013/0006370 | A1* | 1/2013 | Wogoman | A61F 2/4684 623/20.16 |
| 2013/0006376 | A1 | 1/2013 | Wogoman | |
| 2013/0006377 | A1* | 1/2013 | Waite, II | A61B 17/1764 623/20.32 |
| 2013/0261759 | A1* | 10/2013 | Claypool | A61F 2/4657 623/20.33 |
| 2013/0325019 | A1* | 12/2013 | Thomas | A61B 17/157 606/88 |
| 2013/0325136 | A1* | 12/2013 | Thomas | A61B 17/157 623/20.32 |
| 2014/0039636 | A1 | 2/2014 | Kurtz | |
| 2014/0276857 | A1* | 9/2014 | Major | A61F 2/4684 606/88 |

OTHER PUBLICATIONS

GMK Revision, Surgical Technique, Ref. 99.27.12 US Rev. 1, 1999, 74 Pages.

PFC Sigma Knee System, Revision, Surgical Technique, 2000, p. 66.

Smith & Nephew, Legion, Revision Knee System, Surgical Technique, 2005, 40 Pages.

Biomet, Vanguard SSK, Revision System, Surgical Technique, 2008, 64 Pages.

Depuy Orthopaedics, Inc., Sigma Revision and MBT Revision Tray, Surgical Technique, 2008, 82 Pages.

Zimmer Nexgen LCCK, Surgical Technique for Use With LCCK 4-IN-1 Instrument, 2009, 52 Pages.

Sigma Revision and MBT Revision Tray, Surgical Technique, 2012, p. 84.

S-ROM Noiles Rotating Hinge, Surgical Technique, 2012, p. 76.

* cited by examiner

TRIAL KIT FOR KNEE PROSTHESIS SYSTEM

TECHNICAL FIELD

The present disclosure relates generally to an orthopaedic prosthesis, and more particularly to a knee prosthesis. Specifically, the present disclosure relates to a hinged knee prosthesis system.

BACKGROUND

Movement (e.g., flexion and extension) of the natural human knee involves movements of the femur and the tibia. Specifically, during flexion and extension, the distal end of the femur and the proximal end of the tibia articulate relative to one another through a series of complex movements. Damage (e.g., trauma) or disease can deteriorate the bones, articular cartilage, and ligaments of the knee, which can ultimately affect the ability of the natural knee to function in such a manner. As a result, knee prostheses have been developed and implanted into surgically prepared ends of the femur and tibia.

Joint arthroplasty is a well-known surgical procedure by which a diseased and/or damaged natural joint is replaced by a prosthetic joint. A typical knee prosthesis for a total knee replacement, for example, includes a tibial component or tibial tray coupled to the patient's tibia, a femoral component coupled to the patient's femur, and a bearing component positioned between the tibial tray and the femoral component and including a bearing surface to accommodate the condyles of the femoral component.

Orthopaedic surgeons use a variety of orthopaedic surgical instruments in performing joint arthroplasty. These instruments include, for example, provisional components, cutting blocks, drill guides, milling guides and other instruments. Provisional components are intended to be temporarily placed on the prepared bone surfaces prior to permanent fixation of the actual implant components. The provisional components are intended to mimic certain aspects of the permanent prosthetic joint in order for a surgeon to validate measurements, to test several different possible component sizes and shapes, and to evaluate alignment and kinematics by moving the joint with the provisional components in place. Hence, provisional components are aptly known as "trials", and the procedure is known as "trialing."

Figure 1:
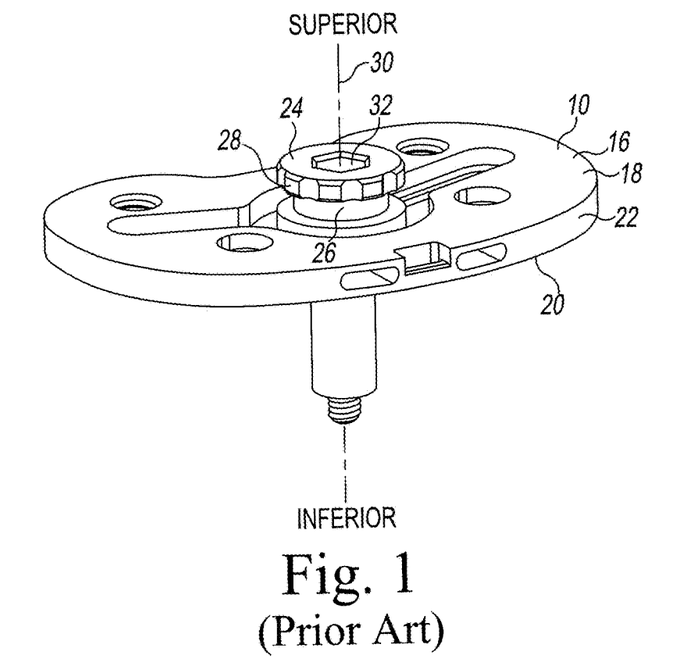
FIG. 1 is a perspective view of a prior art tibial base trial.
Figure 2:
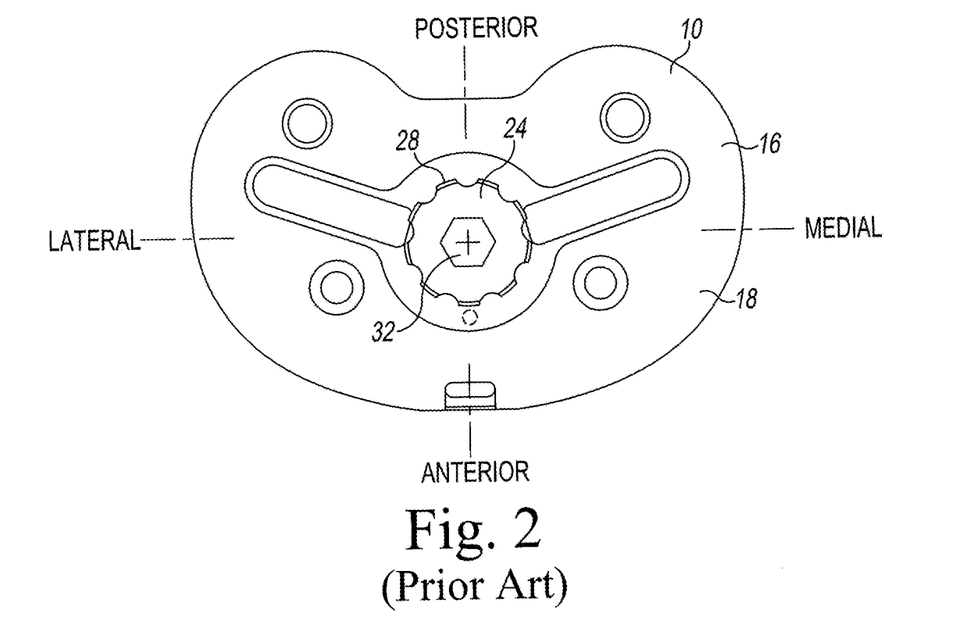
FIG. 2 is a plan view of the prior art tibial base trial of FIG. 1.
Figure 3:
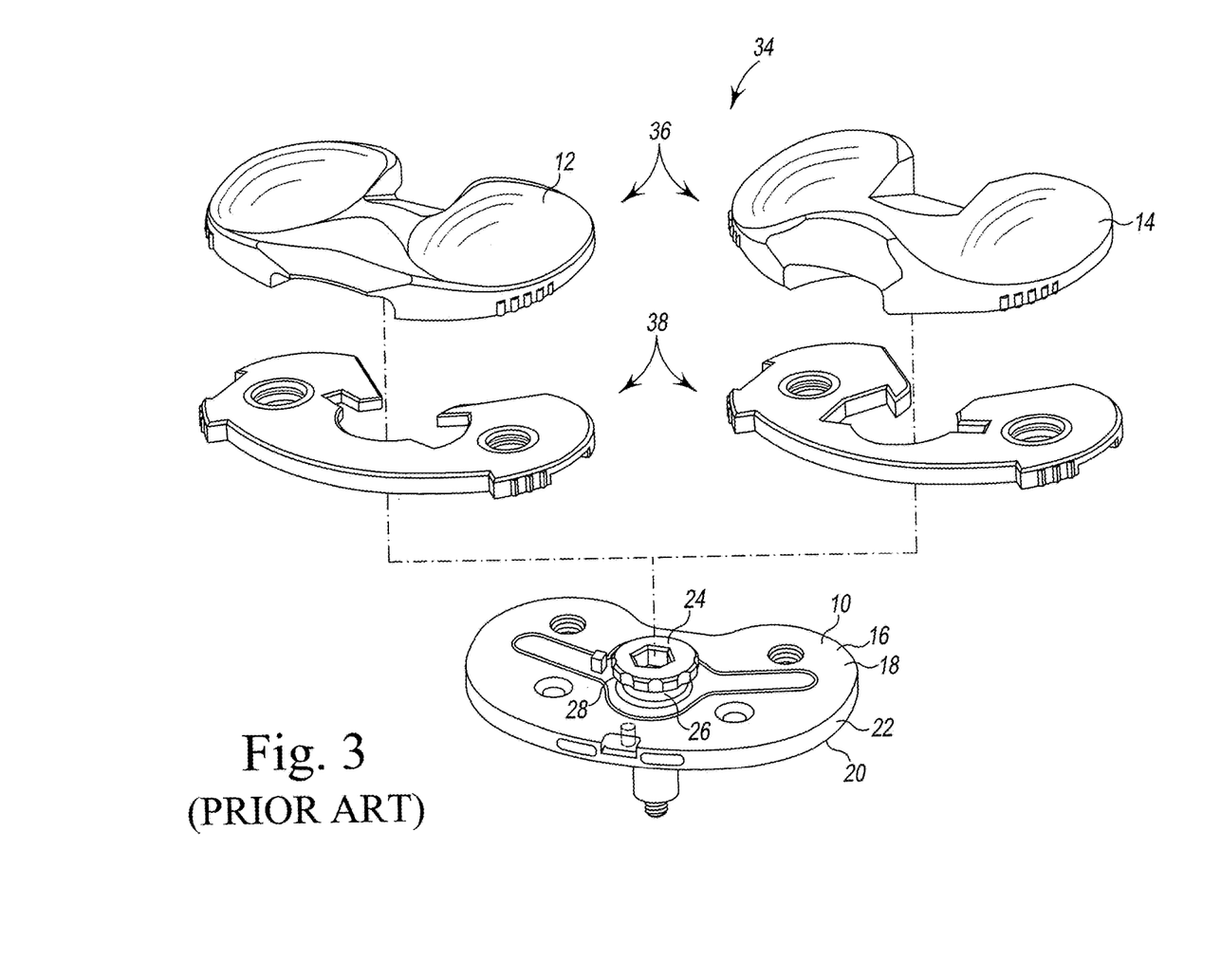
FIG. 3 is an exploded perspective view of a prior art tibial base trial, a prior art base insert and a number of prior art tibial bearing trials.

U.S. Pat. Nos. 9,028,501 and 9,095,356 (incorporated by reference herein in their entireties) illustrate and describe, among other things, tibial trial components. FIGS. 1-3 of the present application are taken from the drawings in those patents to describe trial components developed by the assignee of the present application.

FIG. 1 illustrates a provisional tibial base plate trial 10 that may be used in total knee arthroplasty to size and select the prosthetic components of a knee prostheses that will replace the patient's natural joint. It should be understood that a typical kit would include several sizes of tibial base trial plates 10 along with several sizes of tibial bearing insert trials, shown at 12 and 14 in FIG. 3.

As shown in FIGS. 1-2, the tibial base plate trial 10 includes a plate 16 having an upper surface 18, a lower surface 20, and an outer side wall 22 extending between the surfaces 18, 20. As described in U.S. Pat. Nos. 9,028,501 and 9,095,356, the plate 16 has passageways that permit the advancement of a keel punch and various other instruments into the proximal end of the patient's tibia. It should be understood that the illustrated plate may include all of the features disclosed in those patents.

The tibial base plate trial 10 includes a fastener that includes a button head 24 extending above (superior to) the level of the upper surface 18 of the tibial base plate trial 10. The button head 24 includes a reduced diameter neck 26 and a knob 28 secured to the neck 26. The knob 28 has a knurled outer surface that may be grasped by the surgeon to rotate the fastener about the longitudinal axis 30. The button head 24 also has a socket 32 defined therein, which is sized to receive a driver or other surgical tool to rotate the fastener about the axis 30.

As shown in FIG. 3, the prior art tibial trial system 34 also includes a number of tibial bearing trial assemblies. A tibial bearing trial assembly is disclosed in U.S. Pat. No. 8,968,412 entitled "TRIALING SYSTEM FOR A KNEE PROSTHESIS AND METHOD OF USE," by Thomas E. Wogoman et al., which is incorporated herein by reference. Each illustrated tibial bearing trial assembly is a multi-piece assembly configured to assist the surgeon in selecting a size and configuration of a prosthetic tibial bearing component of the knee prosthesis. A tibial bearing trial may be assembled with one of a number of tibial bearing surface trials 36 and one of a number of a plurality of trial shims 38. Each bearing surface trial 36 has a different size and/or configuration, and each shim 38 has a different thickness. Because each shim 38 is configured to be secured to each bearing surface trial 36, the surgeon is able to assemble a tibial bearing trial of one size and configuration, evaluate the performance of that tibial bearing trial, and then modify the tibial bearing trial as necessary to determine intraoperatively the type and configuration of the prosthetic tibial bearing component to be implanted. It should be appreciated that tibial bearing trial may be a monolithic component, and the system 34 may include multiple tibial bearing trials of different sizes and configurations.

The system 34 may include one or more fixed bearing surface trials and one or more mobile bearing surface trials. Each of these types of trials may be provided as part of a cruciate retaining knee replacement system or as part of a posterior stabilized knee replacement system. For example, in embodiments where the bearing surface trial is embodied as a posterior stabilized trial, the fixed bearing surface trial may include a spine extending upwardly from the upper bearing surface of the trial.

In some cases, the condition of the patient's soft tissue, such as the collateral ligaments, may require use of a more constrained knee prosthesis. One type of constrained knee prosthesis is a hinged knee prosthesis, where the tibial insert and femoral component are connected by a hinge extended transversely through a spine on the tibial insert. In some hinged knee prostheses, it is desirable to allow "pistoning," that is, to allow for the tibial insert to move superiorly and then return to its seated position during flexion and extension of the knee.

To produce an efficient prosthetic knee system that can be used with a patient population having a range of soft tissue conditions, it is desirable to utilize a trial kit that uses the tibial base plate trial such as the prior art plate trial 10 described above with tibial bearing insert trials that are usable in cases where a hinged prosthetic knee system will be used. In addition, it may be desirable to provide such a kit with multiple types of tibial bearing insert trials to allow the surgeon to trial different options intraoperatively.

SUMMARY

The present invention comprises one or more of the features recited in the appended claims or the following features or combinations thereof:

A trial kit for a knee implant system is disclosed. The trial kit includes a tibial base plate trial, an adaptor and a tibial bearing insert trial. The tibial base plate trial has an upper surface, a bottom surface and a button head extending upwardly beyond the upper surface. The button head has a knob and a reduced diameter neck extending from the knob toward the upper surface of the tibial base plate trial. The adaptor has a base including an upper surface, a lower surface spaced from the upper surface, a posterior face, an anterior face, and side surfaces between the upper and lower surfaces. The adaptor further includes an elongate post extending upwardly from the upper surface of the base to a superior end. The elongate post has a superior-inferior central longitudinal axis and a substantially cylindrical shape for a substantial portion of its length. The base of the adaptor has surfaces defining an adaptor channel in its lower surface extending from a posterior opening in the posterior face of the base in an anterior direction. The surfaces defining the adaptor channel are sized and shaped to define an undercut and are sized and shaped so that the adaptor can be mounted on the tibial base plate trial by sliding the adaptor in a posterior direction on the upper surface of the base plate trial until the knob of the button head is received in the adaptor channel. The sizes and shapes of the undercut in the adaptor channel and the knob and reduced diameter neck prevent the adaptor from lifting off the tibial base plate trial. The tibial bearing insert trial has a superior articulation surface, a spine extending superiorly beyond the superior articulation surface, and an inferior surface having a recess to receive the base of the adaptor. The tibial bearing insert trial has a surface within the recess defining an upper recess surface. The upper recess surface has an opening that leads to a first insert channel in the spine of the tibial bearing insert trial. At least a portion of the first insert channel is sized, shaped and oriented to receive the elongate post of the adaptor to mount the tibial bearing insert trial on the adaptor and to allow the tibial bearing insert trial to move in a superior direction with respect to the adaptor. The tibial bearing insert trial can be assembled with the adaptor by inserting the superior end of the elongate post into the opening in the upper recess surface of the tibial bearing insert trial. The assembly of the tibial bearing insert trial and the adaptor can be mounted on the tibial base plate trial by sliding the assembly in a posterior direction on the upper surface of the tibial base plate trial until the button head is received within the adaptor channel.

The side surfaces of the base of the adaptor define a base shape and the recess in the tibial bearing insert trial and the base of the adaptor may have similar shapes.

The adaptor channel may have a blind anterior end. In such embodiments, the adaptor can be mounted on the tibial base plate trial by sliding the adaptor in a posterior direction on the upper surface of the tibial base plate trial until the knob of the button head is positioned at the blind anterior end of the adaptor channel.

The adaptor may include a resilient clip sized, shaped and positioned to engage the reduced diameter neck of the button head of the tibial base plate trial.

When the assembly of the tibial bearing insert trial and the adaptor is mounted on the tibial base plate trial, the fit of the button head in the adaptor channel prevents the assembly from moving superiorly on the tibial base plate trial.

The elongate post of the adaptor may include a cross-piece extending transversely from the elongate post in a direction perpendicular to the central longitudinal axis. In this embodiment, the opening in the upper surface of the recess of the tibial bearing insert trial includes a rectangular portion and a second opening leads from the first insert channel to a second insert channel. The first and second insert channels are defined by internal surfaces. In this embodiment, the second opening has a circular portion coaxial with the circular portion of the first opening and a rectangular portion. In this embodiment, the tibial bearing insert trial can be assembled with the adaptor by inserting the superior end of the elongate post into the opening in the upper recess surface of the tibial bearing insert trial so that the cross-piece of the elongate post is received in the first insert channel, turning the adaptor relative to the tibial bearing insert trial about the central longitudinal axis of the elongate post and advancing the cross-piece of the elongate post through the second opening and into the second insert channel. In this embodiment, the first and second openings are sized, shaped and oriented so that the cross-piece of the elongate post must be oriented in different directions to pass through the first and second openings.

In this embodiment, the first and second insert channels and the elongate post may be sized and shaped so that the tibial bearing insert trial can move superiorly with respect to the adaptor for a limited distance.

In this embodiment, the assembly of the tibial bearing insert trial and the adaptor can rotate on the tibial base plate trial while the button head is received within the adaptor channel.

In this embodiment, the first opening includes rectangular portions defined by edges separated by a plane that extends in one direction and the second opening includes rectangular portions defined by edges separated by a plane that extends in a different direction. In this embodiment, the edges of the rectangular portions of the first opening may be separated by a plane that extends in an anterior-posterior direction and the edges of the rectangular portions of the second opening may be separated by a plane that extends in a medial-lateral direction.

BRIEF DESCRIPTION OF THE DRAWINGS

The Background and detailed description particularly refer to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise. For reference purposes, the superior and inferior directions are labeled with respect to the axis 30 in FIG. 1, and the anterior, posterior, medial and lateral directions are labeled on FIG. 2.

Figure 4:
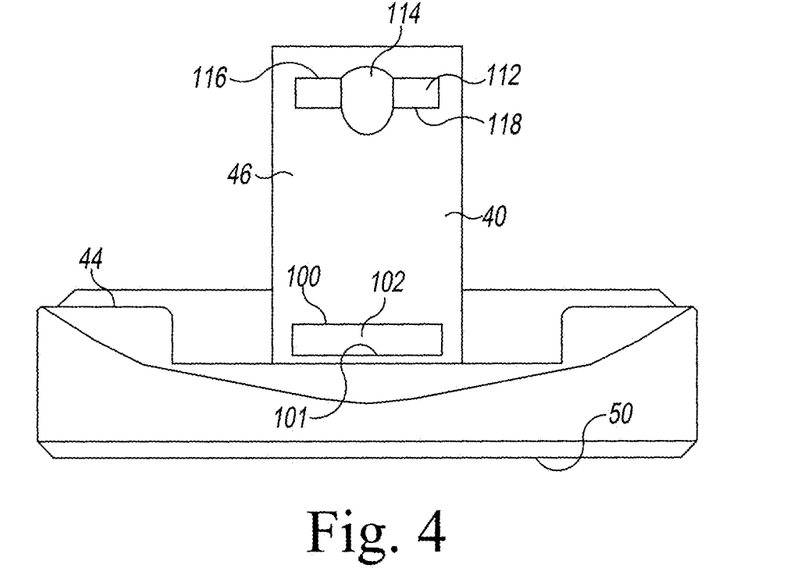
FIG. 4 is a front view of a tibial bearing insert trial that may be used as part of the knee prosthesis trial kit of the present invention.
Figure 5:
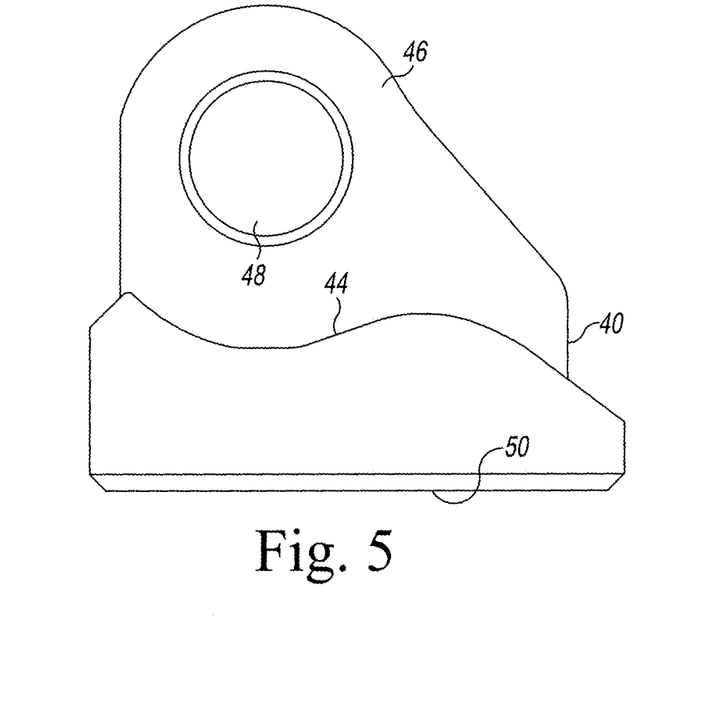
FIG. 5 is a side view of the tibial bearing insert trial of FIG. 4.
Figure 6:
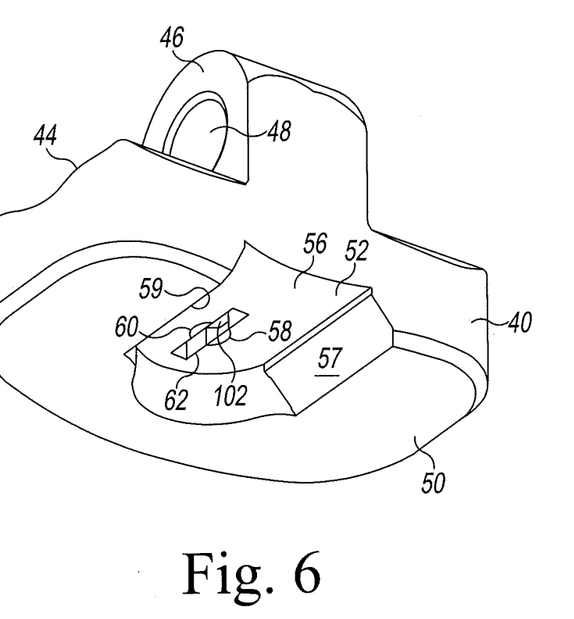
FIG. 6 is a perspective view of the tibial bearing insert trial of FIGS. 4-5, illustrating the inferior side of the trial.
Figure 7:
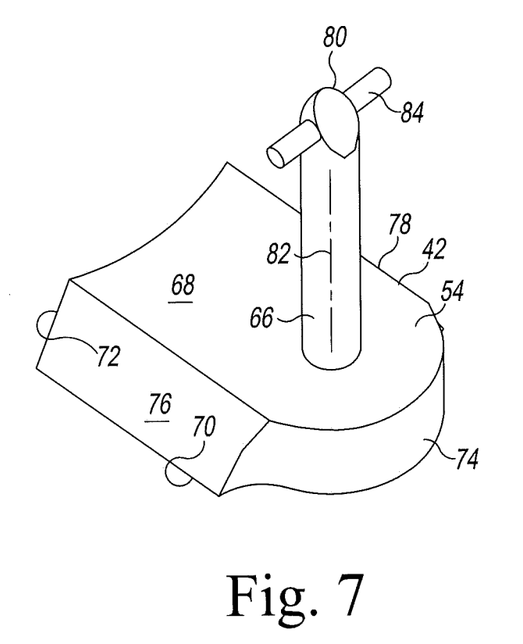
FIG. 7 is a perspective view of an adaptor that may be used as part of the knee prosthesis trial kit of the present invention, illustrating the superior side of the adaptor.
Figure 8:
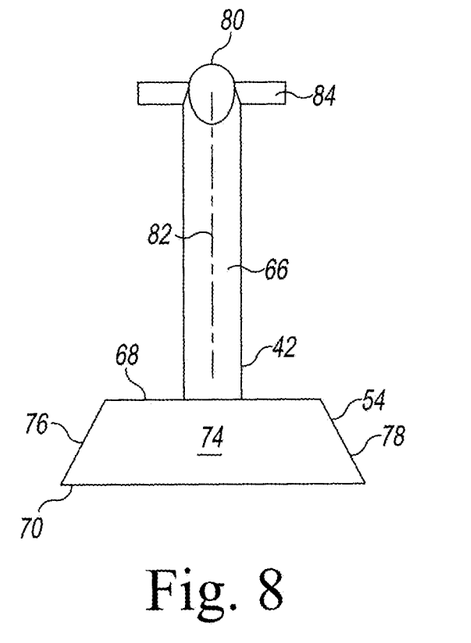
FIG. 8 is a front or anterior view of the adaptor of FIG. 7.

Referring now to FIGS. 4-6, parts of a trial kit for a prosthetic knee implant system are illustrated. The illustrated trial kit parts comprise a tibial bearing insert trial 40 and an adaptor 42 that may be used with the tibial base plate trial 10 of FIGS. 1-3 (described above), as an alternative to the use of the tibial bearing surface trial and shim 36, 38 of the prior art.

The illustrated adaptor and tibial bearing insert trial 40 are intended for use as part of a hinged knee prosthesis system.

As shown in FIGS. 4-6, the tibial bearing insert trial 40 has a superior articulation surface 44, a spine 46 extending superiorly beyond the superior articulation surface. The spine 46 has a cylindrical hole 48 extending through it in a medial-lateral direction. The hole 48 is provided to receive a hinge pin of a femoral component (not shown) for a hinged knee prosthesis system. As shown in FIG. 6, the tibial bearing insert trial 40 has an inferior surface 50 having a recess 52. As described in more detail below, the recess 52 is shaped to receive a base 54 of the adaptor 42; that is, the recess 52 and the base 54 of the adaptor 42 have similar shapes.

As shown in FIG. 6, the tibial bearing insert trial 40 has a surface within the recess 52 defining an upper recess surface 56. The upper recess surface 56 has an opening 58 with a substantially circular portion 60 and rectangular portions 62 extending in a generally anterior-posterior direction. The opening 58 leads to channels extending into the spine 46 of the tibial insert trial 40. As described in more detail below, portions of the channels are sized and cylindrically shaped to receive a post 66 of the adaptor 42 to mount the bearing insert trial 40 on the adaptor 42. Angled side surfaces 57, 59 also define the medial and lateral sides of the recess 52.

As shown in FIGS. 7-10, the base 54 of the adaptor 42 an upper surface 68, a lower surface 70 spaced from the upper surface 68, a posterior face 72, an anterior face 74, and side surfaces 76, 78 between the upper and lower surfaces 68, 70. The side surfaces define the shape of the perimeter of the base. The elongate post 66 extends upwardly from the upper surface 68 of the base 54 to a superior end 80. The elongate post 66 has a superior-inferior central longitudinal axis 82, a substantially cylindrical shape for a substantial portion of its length and a cross-piece 84 extending transversely (medial-lateral in the illustrated embodiment) from the elongate post 66 in a direction perpendicular to the central longitudinal axis 82.

Figure 9:
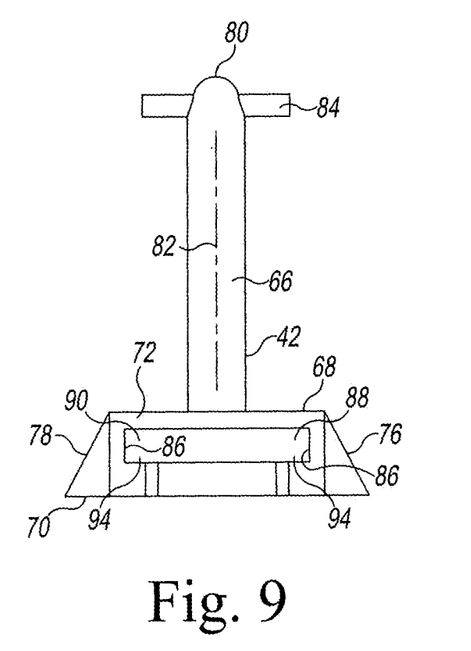
FIG. 9 is a back or posterior view of the adaptor of FIGS. 7-8.
Figure 10:
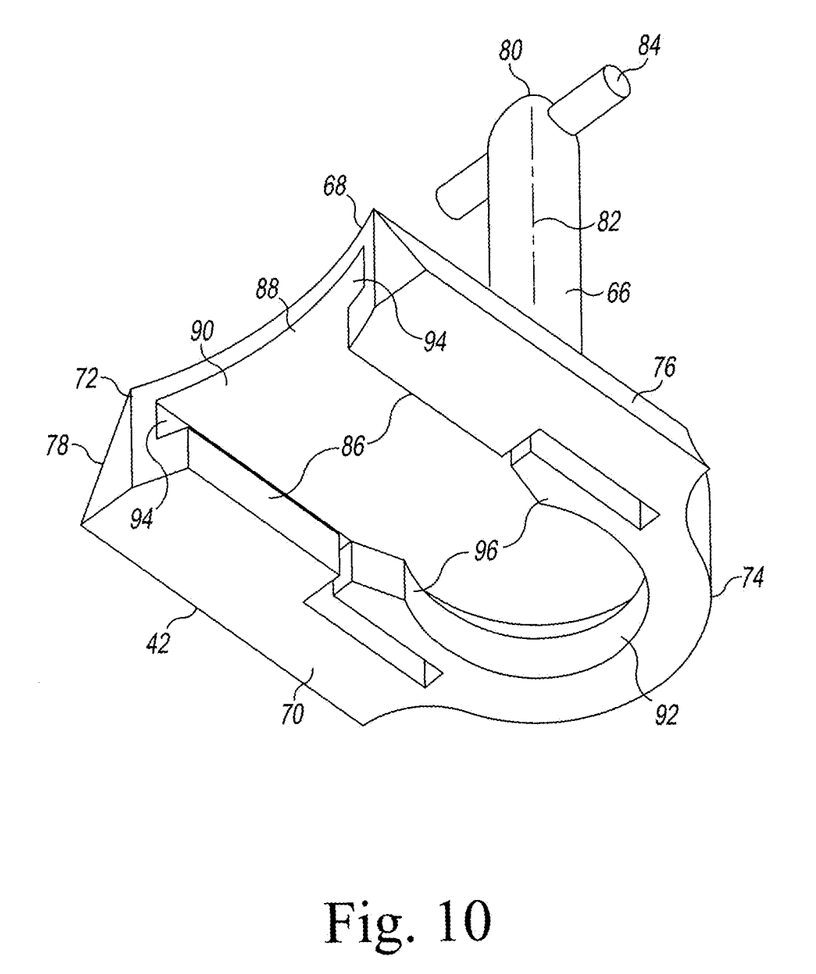
FIG. 10 is a perspective view of the adaptor of FIGS. 7-9, illustrating the inferior side of the adaptor.

As shown in FIGS. 9-10, the base 54 of the adapter 42 has surfaces 86 defining an adaptor channel 88 in its lower surface 70 extending from a posterior opening 90 in the posterior face 72 of the base in an anterior direction to blind anterior end 92. The surfaces 86 defining the adaptor channel 88 are sized and shaped to define opposite undercuts 94 and are sized and shaped so that the adaptor can be mounted on the tibial base plate 10 trial by sliding the adaptor 42 in a posterior direction on the upper surface 18 of the base plate trial 10 until the knob 28 of the button head 24 is received in the adaptor channel 88 and positioned at the blind anterior end 92 of the adaptor channel 88. The sizes and shapes of the undercut 94 in the adaptor channel 88 and the knob 28 and reduced diameter neck 26 prevent the adaptor 42 from lifting off the tibial base plate trial 10. As shown in FIG. 10, the illustrated adaptor also includes arms 96 defining a resilient clip. The clip is sized, shaped and positioned to engage the reduced diameter neck 26 of the button head 24 of the tibial base plate trial 10. This mounting of the adaptor 42 on the tibial base plate trial 10 is illustrated in FIGS. 11-14.

FIGS. 11-14 also illustrate the assembly of the adaptor 42 and the tibial bearing insert trial 40. Generally, the post 66 and its cross-piece 84 cooperate with perpendicular channels in the tibial bearing insert trial 40 to hold the components 42, 40 together as an assembly while allowing for pistoning movement—that is, movement in a superior direction away from the tibial base plate trial 10.

As shown in FIGS. 4 and 11-13, the tibial bearing insert trial has a pair of spaced surfaces 100, 101 that are generally parallel to each other and to the inferior surface of the trial 40. These surfaces 100, 101 are located in the spine 46 and define a first insert channel 102. From the inferior side of the trial 40, there is a single entrance/exit to this first insert channel 102: the opening 58 in the recess 52. Since the rectangular portions 62 of the opening 58 extend in the anterior-posterior direction, the adapter must be turned so that the cross-piece 84 of the post 66 extends in an anterior-posterior direction with respect to the insert trial 40 for the cross-piece 84 to enter the first insert channel 102.

Figure 11:
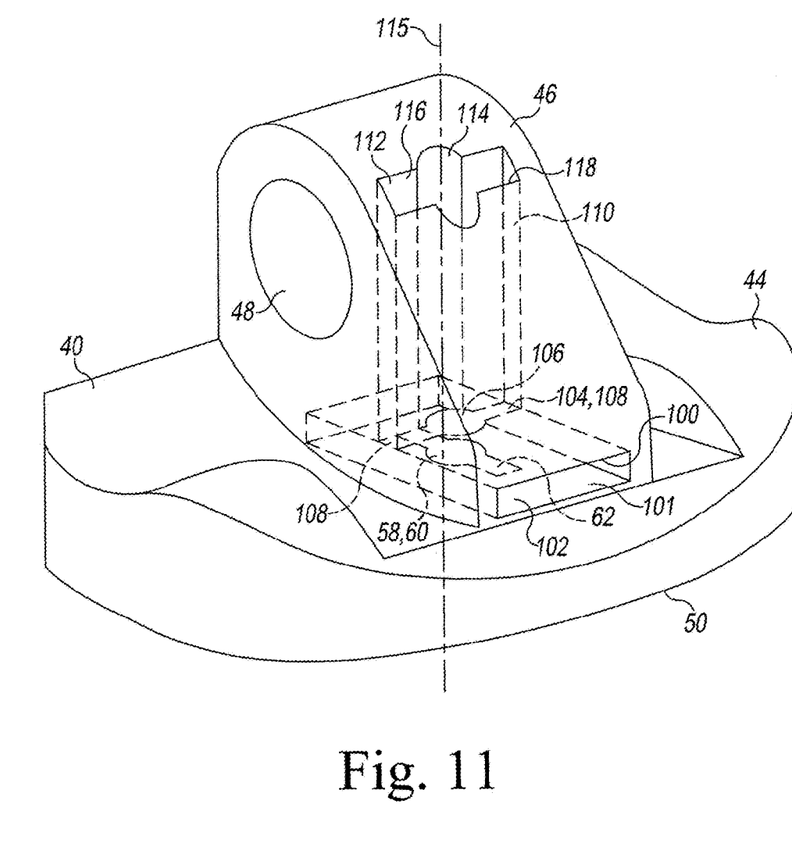
FIG. 11 is a perspective view of the trial bearing insert of FIGS. 4-6, illustrating in phantom the channels and openings that receive parts of the adaptor.

As shown in FIG. 11, the upper surface 100 that defines the first insert channel 102 also has an opening 104 with a circular portion 106 that is co-axial with the circular portion 60 of the opening 58 in the recess 52. The opening 104 also has rectangular portions 108 that extend in a generally medial-lateral direction. The opening 104 leads to a second insert channel 110 that extends in a superior direction further into the spine 46 of the tibial insert trial 40. The second insert channel 110 extends through the spine 46 in the illustrated embodiment to a superior opening 112.

A portion of the second insert channel 110 is cylindrically shaped to receive part of the post 66; the cylindrical portion 114 is coaxial with the circular openings 60, 106. The common axis is shown at 115 in FIGS. 11-14. Spaced parallel interior surfaces 116, 118 extend in a generally medial-lateral direction and perpendicular to the plane of the inferior surface 50 of the tibial bearing insert trial. These surfaces 116, 118 define spaces that receive the cross-piece 84 of the post 66 of the adaptor 42 and limit rotation of the post within the cylindrical portion 114 of the second insert channel 110.

The upper recess surface 56 has an opening 58 with a substantially circular portion 60 and rectangular portions 62 extending in a generally medial-lateral direction. The opening 58 leads to a channel 64 extending in a superior direction into the spine 46 of the tibial insert trial 40. A portion of the channel 64 is sized and cylindrically shaped to receive a post 66 of the adaptor 42 to mount the bearing insert trial 40 on the adaptor 42.

To use the trial kit of the present invention, the surgeon would resect the tibial and femoral surfaces to prepare the bones to receive the implants. A tibial base plate trial such as plate 10 may be placed on the resected proximal surface of the tibia in the manner described in U.S. Pat. Nos. 9,028,501 and 9,095,356. If the surgeon determines that the condition of the patient's soft tissue warrants use of a hinged prosthetic implant, the surgeon may select an appropriate size of tibial bearing insert trial 40 and an adaptor 42 from the surgical kit.

Figure 12:
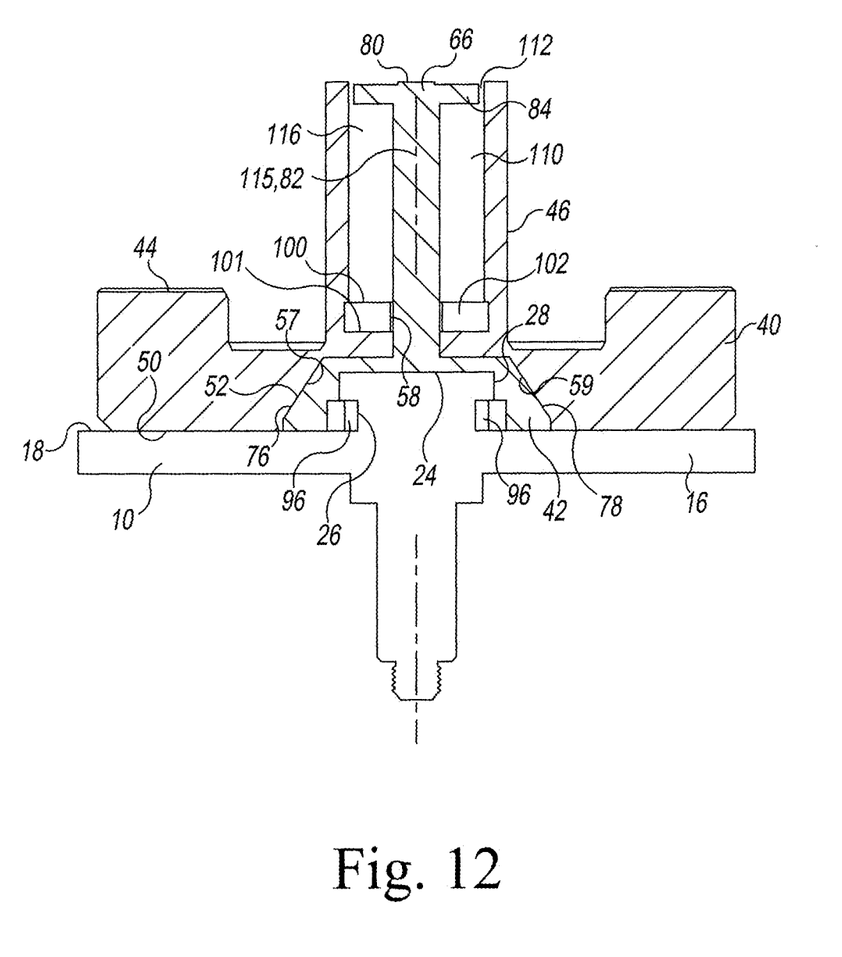
FIG. 12 is a front view of an assembly of the trial tibial base plate of FIGS. 1-3 with the tibial bearing trial of FIGS. 4-6 and 11 and the adaptor of FIGS. 7-10, with the tibial bearing insert trial and adaptor being shown in a cross section taken along a medial-lateral plane through the channels of the tibial bearing trial and the post of the adaptor, and illustrating the tibial bearing insert trial in a seated position.
Figure 13:
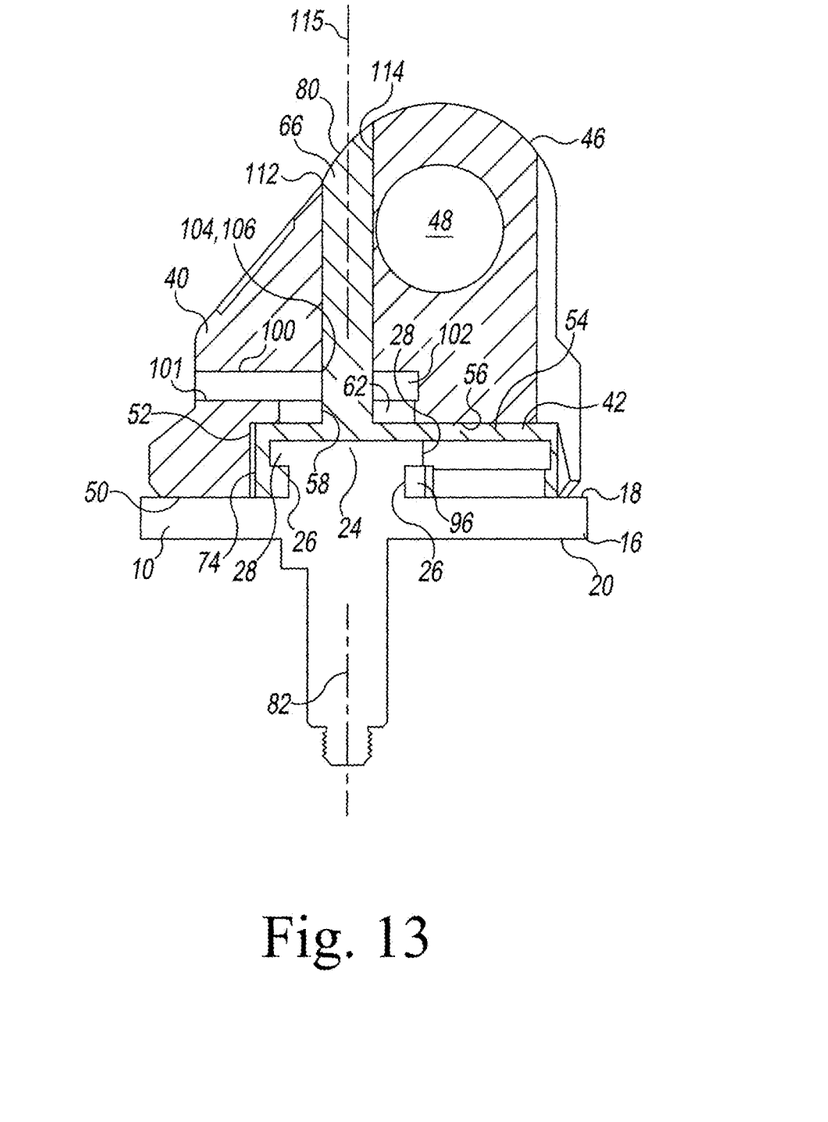
FIG. 13 is a side view of the assembly of FIG. 12, with the cross section being taken along an anterior-posterior plane through the channels of the tibial bearing insert trial and post of the adaptor.

The surgeon may assemble the tibial bearing insert trial 40 with the adaptor 42 by turning the adaptor to align the cross-pieces 84 in an anterior-posterior direction and inserting the superior end 80 of the elongate post 66 into the opening 58 in the upper recess surface 56 of the tibial bearing insert trial 40. The cross-pieces 84 of the elongate post 66 are moved through the rectangular portions 62 of the opening 58 and are received in the more inferior first insert channel 102 between the spaced surfaces 100, 101. The surgeon may then turn the adaptor 42 relative to the tibial bearing insert trial 40 a quarter turn (ninety degrees) to align the cross-pieces 84 (within the first insert channel 102) along a medial-lateral axis. The cross-pieces 84 of the elongate post 66 are then advanced through the second more superior opening 104, with the post 66 advancing through the circular portion 106 into the cylindrical portion 114 and the cross-pieces 84 advancing through the rectangular portions 108 of the opening 104 into the space between the parallel surfaces 116, 118 until the superior end of the post 66 reaches the superior opening 112 and the tibial bearing insert trial 40 is seated on the adaptor 42 as shown in FIGS. 12-13. So assembled, the tibial bearing insert trial cannot rotate about the axes 82, 115 because of the limited spaced provided by the interior surfaces 116, 118; essentially, the spacing of the surfaces 116, 118 limit relative movement between the tibial bearing insert trial 40 and the adaptor 42 to superior-inferior movement.

The first and second openings 58, 104 are sized, shaped and oriented so that the cross-piece 84 of the elongate post must be oriented in different directions to pass through the first and second openings 58, 104. In the illustrated embodiment, the rectangular portions 62 of the first opening are defined by edges that are separated by a plane that extends in the anterior-posterior direction and the rectangular portions 108 of the second opening 104 are oriented at a right angle to those of the first opening so that the edges of the rectangular portions 108 of the second opening 104 are separated by a plane that extends in a medial-lateral direction. It should be understood that these shapes are orientations are exemplary and that other shapes and orientations may be used and still achieve the desired result of providing a bearing insert trial and adaptor that can be easily assembled and disassembled, allow for controlled superior-inferior movement and that will not be inadvertently separated intraoperatively.

The surgeon may then mount the assembly (as shown in FIGS. 12-13) of the tibial bearing insert trial 40 and the adaptor 42 on the tibial base plate trial 10 by sliding the assembly in a posterior direction on the upper surface 18 of the tibial base plate trial 10 until the button head 24 is received within the adaptor channel 88. In moving the assembly past the button head, the neck 26 of the button head 24 passes through the arms 96 of the resilient clip, which then engage neck of the button head and prevent the assembly from moving off of the tibial base plate trial until the surgeon purposefully pulls the assembly in an anterior direction.

Figure 14:
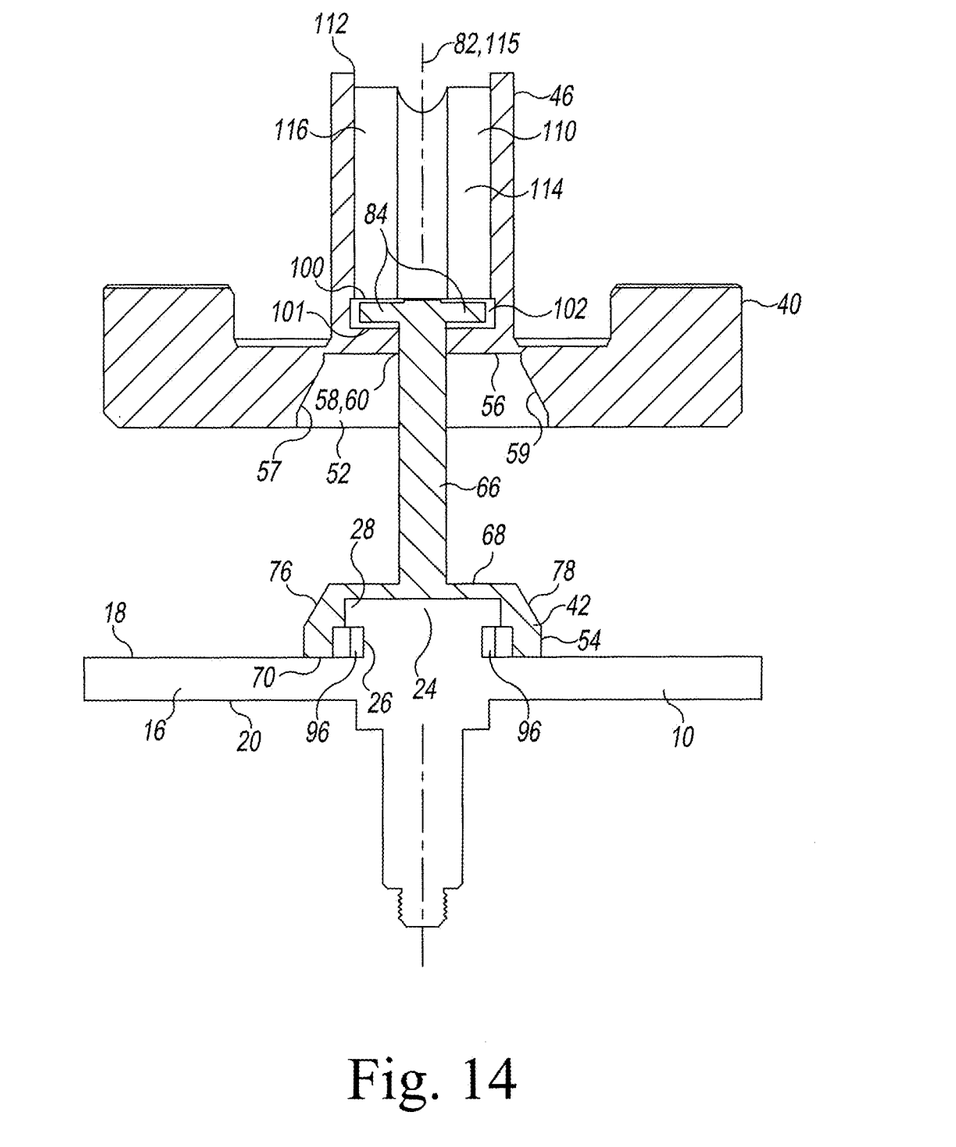
FIG. 14 is a front view of the assembly of FIGS. 12-13 illustrating the tibial bearing insert trial in a fully extended position.

Once the assembly is mounted on the tibial base plate trial, the surgeon may conduct standard evaluation procedures used when trialing an implant. Advantageously, the surgeon may move the knee through a range of motion and observe pistoning of the tibial bearing insert trial with respect to the tibial base plate trial. In other words, the hinged connection between the femoral trial (not shown) and the tibial bearing insert trial may pull the tibial bearing insert trial superiorly with respect to the adaptor (which is fixed on the tibial base plate trial) while movement of the tibial bearing insert trial is controlled by the interaction of the elongate post and the channel. Superior movement of the tibial bearing insert trial is stopped when the cross-piece engages the surface defining the inferior end of the second cuboid-shaped portion of the channel. This position is illustrated in FIG. 14. Although the interior surfaces 116, 118 prevent rotation of the tibial bearing insert trial 40 with respect to the adaptor 42, the engagement of the resilient clip on the neck of the button head allows for rotation of the assembly with respect to the tibial base plate trial about a superior-inferior axis through the button head.

Once the trialing is complete, the surgeon may remove the assembly of the tibial bearing insert trial and the adaptor from the tibial base plate trial by sliding the assembly in an anterior direction on the upper surface of the tibial base plate trial until the button head is no longer within the adaptor channel. In moving the assembly past the button head, the neck of the button head passes through the arms of the resilient clip, which then disengage from the neck of the button head. The assembly may then be disassembled by moving the adaptor inferiorly with respect to the tibial bearing insert trial, turning the adapter a quarter turn to align the cross-piece with the rectangular portion of the opening and then separating the adaptor and tibial bearing insert trial.

Thus, the present invention allows for trialing a hinged knee prosthesis and allows for pistoning of the trial bearing insert as the patient's knee is moved through flexion and extension. In addition, the manner of connecting the adaptor and the bearing insert trial provides the desired range of motion in the superior-inferior direction while holding the components together to prevent inadvertent separation of the components intraoperatively.

It should be understood however that a surgical kit need not incorporate all of the features of the present invention. For example, an adaptor could be provided with an elongate post but without cross-pieces and the tibial bearing insert trial could only have a cylindrical channel; such an embodiment would allow the trial to piston but would not necessarily prevent inadvertent separation of the components.

A trial kit embodying the invention may include several different sizes of tibial bearing insert trials. Different sizes of tibial bearing insert trials may include commonly sized recesses, openings and channels so that a single adaptor may be used with several different sizes of tibial bearing insert trials. In addition, a trial kit incorporating the teachings of the present invention could include all of the prior art trial components illustrated in FIG. 3 in combination with the trial bearing insert trial 40 and adaptor 42 of the present invention to allow the surgeon intraoperative flexibility in the choice of the level of constraint to use with the patient. Moreover, although the illustrated adaptor 42 allows for rotation of the tibial bearing insert trial 40 with respect to the tray trial 10, the adaptor 42 or insert trial 40 may be modified to trial for a fixed bearing option if desired.

Moreover, while the disclosure has been illustrated and described in detail in the drawings and foregoing description, the illustration and description are intended to be considered as exemplary and not restrictive in character. All changes and modifications that come within the spirit of the disclosure are desired to be protected.

We claim:

1. A trial kit for a knee implant system, wherein the trial kit includes:
   a tibial base plate trial, an adaptor and a tibial bearing insert trial;
   wherein
   the tibial base plate trial has an upper surface, a bottom surface, a button head extending upwardly beyond the upper surface, the button head having a knob and a reduced diameter neck extending from the knob toward the upper surface of the tibial base plate trial;
   the adaptor has a base including an upper surface, a lower surface spaced from the upper surface, a posterior face, an anterior face, and side surfaces between the upper and lower surfaces;
   the adaptor further includes an elongate post extending upwardly from the upper surface of the base to a superior end, the elongate post having a superior-inferior central longitudinal axis and a substantially cylindrical shape for a substantial portion of its length;
   the base of the adaptor has surfaces defining an adaptor channel in its lower surface extending from a posterior opening in the posterior face of the base in an anterior direction;
   the surfaces defining the adaptor channel are sized and shaped to define an undercut and are sized and shaped so that the adaptor can be mounted on the tibial base plate trial by sliding the adaptor in a posterior direction on the upper surface of the base plate trial until the knob of the button head is received in the adaptor channel, the sizes and shapes of the undercut in the adaptor channel and the knob and reduced diameter neck preventing the adaptor from lifting off the tibial base plate trial;
   the tibial bearing insert trial has a superior articulation surface, a spine extending superiorly beyond the superior articulation surface, and an inferior surface having a recess to receive the base of the adaptor;
   the tibial bearing insert trial has a surface within the recess defining an upper recess surface;
   the upper recess surface has an opening;
   the opening leads to a first insert channel in the spine of the tibial bearing insert trial;
   at least a portion of the first insert channel is sized, shaped and oriented to receive the elongate post of the adaptor to mount the tibial bearing insert trial on the adaptor and allow for the tibial bearing insert trial to move in a superior direction with respect to the adaptor;
   the tibial bearing insert trial can be assembled with the adaptor by inserting the superior end of the elongate post into the opening in the upper recess surface of the tibial bearing insert trial;
   the assembly of the tibial bearing insert trial and the adaptor can be mounted on the tibial base plate trial by sliding the assembly in a posterior direction on the upper surface of the tibial base plate trial until the button head is received within the adaptor channel.

2. The trial kit of claim 1 wherein the side surface of the base of the adaptor define a base shape and the recess in the tibial bearing insert trial and the base of the adaptor have similar shapes.

3. The trial kit of claim 1 wherein the adaptor channel has a blind anterior end and the adaptor can be mounted on the tibial base plate trial by sliding the adaptor in a posterior direction on the upper surface of the tibial base plate trial until the knob of the button head is positioned at the blind anterior end of the adaptor channel.

4. The trial kit of claim 1 wherein the adaptor includes a resilient clip sized, shaped and positioned to engage the reduced diameter neck of the button head of the tibial base plate trial.

5. The trial kit of claim 1 wherein when the assembly of the tibial bearing insert trial and the adaptor is mounted on the tibial base plate trial, the fit of the button head in the adaptor channel prevents the assembly from moving superiorly on the tibial base plate trial.

6. The trial kit of claim 1 wherein:
   the elongate post of the adaptor includes a cross-piece extending transversely from the elongate post in a direction perpendicular to the central longitudinal axis;
   the opening in the upper surface of the recess of the tibial bearing insert trial includes a rectangular portion;
   the first insert channel is defined by internal surfaces;
   a second opening leads from the first insert channel to a second insert channel defined by internal surfaces in the spine of the tibial bearing insert trial;
   the second opening has a circular portion coaxial with the circular portion of the first opening and a rectangular portion;
   the tibial bearing insert trial can be assembled with the adaptor by inserting the superior end of the elongate post into the opening in the upper recess surface of the tibial bearing insert trial so that the cross-piece of the elongate post is received in the first insert channel, turning the adaptor relative to the tibial bearing insert trial about the central longitudinal axis of the elongate post and advancing the cross-piece of the elongate post through the second opening and into the second insert channel; and
   the first and second openings are sized, shaped and oriented so that the cross-piece of the elongate post must be oriented in different directions to pass through the first and second openings.

7. The trial kit of claim 6 wherein the first and second insert channels and the elongate post are sized and shaped so that the tibial bearing insert trial can move superiorly with respect to the adaptor for a limited distance.

8. The trial kit of claim 6 wherein the assembly of the tibial bearing insert trial and the adaptor can rotate on the tibial base plate trial while the button head is received within the adaptor channel.

9. The trial kit of claim 6 wherein the first opening includes rectangular portions defined by edges separated by a plane that extends in one direction and the second opening includes rectangular portions defined by edges separated by a plane that extends in a different direction.

10. The trial kit of claim 9 wherein the edges of the rectangular portions of the first opening are separated by a plane that extends in an anterior-posterior direction and the edges of the rectangular portions of the second opening are separated by a plane that extends in a medial-lateral direction.

* * * * *